(12) United States Patent
Sprague et al.

(10) Patent No.: US 8,747,779 B2
(45) Date of Patent: Jun. 10, 2014

(54) MICROFLUIDIC CLINICAL ANALYZER

(75) Inventors: Isaac Sprague, Bellevue, WA (US); John E. Emswiler, Renton, WA (US); C. Frederick Battrell, Redmond, WA (US); Joan Haab, Seattle, WA (US); Sean M. Pennell, Seattle, WA (US); Justin L. Kay, Renton, WA (US); Zane B. Miller, Seattle, WA (US); Troy D. Daiber, Auburn, WA (US)

(73) Assignee: Micronics, Inc., Redmond, WA (US)

( * ) Notice: Subject to any disclaimer, the term of this patent is extended or adjusted under 35 U.S.C. 154(b) by 0 days.

(21) Appl. No.: 13/273,085

(22) Filed: Oct. 13, 2011

(65) Prior Publication Data

US 2012/0156112 A1 Jun. 21, 2012

Related U.S. Application Data

(63) Continuation of application No. PCT/US2010/030901, filed on Apr. 13, 2010.

(60) Provisional application No. 61/168,840, filed on Apr. 13, 2009.

(51) Int. Cl.
*B01L 3/00* (2006.01)

(52) U.S. Cl.
USPC ....... 422/503; 422/52; 422/82.05; 422/82.06; 422/82.07; 422/82.08; 422/82.09; 422/82.11; 422/407; 422/501; 422/502; 435/164; 435/165; 435/283.1; 435/287.1; 435/287.2; 435/288.7; 435/808; 435/4; 435/5; 435/7.2; 435/7.9; 436/164; 436/165; 436/172; 436/174; 436/518; 436/805; 436/809

(58) Field of Classification Search
USPC ............... 422/52, 82.05, 82.06, 82.07, 82.08, 422/82.09, 82.11, 407, 501, 502, 503; 436/164, 165, 172, 174, 518, 805, 809; 435/164, 165, 283.1, 287.1, 287.2, 435/288.7, 808, 4, 5, 7.2, 7.9
See application file for complete search history.

(56) References Cited

U.S. PATENT DOCUMENTS

| | | | |
|---|---|---|---|
| 6,001,307 A | 12/1999 | Naka et al. | |
| 6,325,975 B1 | 12/2001 | Naka et al. | |
| 2004/0241788 A1* | 12/2004 | Wainwright et al. | 435/34 |
| 2005/0129582 A1* | 6/2005 | Breidford et al. | 422/100 |
| 2007/0042427 A1* | 2/2007 | Gerdes et al. | 435/7.1 |
| 2007/0190525 A1* | 8/2007 | Gu et al. | 435/5 |
| 2008/0081341 A1 | 4/2008 | Maher et al. | |
| 2009/0017483 A1 | 1/2009 | Yamaoka et al. | |

FOREIGN PATENT DOCUMENTS

| | | |
|---|---|---|
| EP | 1 180 135 B1 | 8/2005 |
| JP | 52-55679 A | 5/1977 |
| JP | 2003-207454 A | 7/2003 |
| JP | 2004-333452 A | 11/2004 |
| JP | 2006-90774 A | 4/2006 |
| JP | 2006-517029 A | 7/2006 |
| JP | 2006-520190 A | 9/2006 |

(Continued)

*Primary Examiner* — Dennis M White
(74) *Attorney, Agent, or Firm* — Seed IP Law Group PLLC (57) ABSTRACT

A microfluidic cartridge including on-board dry reagents and microfluidic circuitry for determining a clinical analyte or analytes from a few microliters of liquid sample; with docking interface for use in a host workstation, the workstation including a pneumatic fluid controller and spectrophotometer for monitoring analytical reactions in the cartridge.

14 Claims, 6 Drawing Sheets

(56) References Cited

FOREIGN PATENT DOCUMENTS

| | | | |
|---|---|---|---|
| JP | 2007-514142 A | 5/2007 | |
| JP | 2008-503722 A | 2/2008 | |
| JP | 2008-89597 A | 4/2008 | |
| JP | 2008-96375 A | 4/2008 | |
| JP | 2009-14529 A | 1/2009 | |
| JP | 2009-513966 A | 4/2009 | |
| WO | 2005/066638 A1 | 7/2005 | |
| WO | 2006/035830 A1 | 4/2006 | |
| WO | 2007/049009 A1 | 5/2007 | |
| WO | WO 2007106579 A2 * | 9/2007 | |
| WO | WO 2009037361 A1 * | 3/2009 | |

* cited by examiner

MICROFLUIDIC CLINICAL ANALYZER

CROSS-REFERENCE TO RELATED APPLICATIONS

This application is a continuation of International PCT Patent Application No. PCT/US2010/030901, which was filed on Apr. 13, 2010, now pending, which claims the benefit under 35 U.S.C. §119(e) of U.S. Provisional Patent Application No. 61/168,840, filed Apr. 13, 2009, which applications are incorporated herein by reference in their entireties.

BACKGROUND

1. Field

The present invention is in the field of microfluidic devices, and relates to a microfluidic device and apparatus for performance of clinical laboratory assays.

2. Description of the Related Art

Clinicians routinely rely on laboratory testing to better assess the condition of patients under their care. Large clinical analyzers such as the "robot chemist" (U.S. Pat. No. 3,193,358), Technicon AutoAnalyzer, and Automatic Clinical Analyzer (Dupont, Wilmington Del.) are well known. A step toward miniaturization of clinical assays is taken in U.S. Pat. No. 3,799,742 to Coleman.

But microfluidic chips have yet greater advantages of reduced scale and are adapted for receiving microliter or nanoliter-sized samples. However, as noted by Lilja in U.S. Pat. No. 4,088,448, mixing of reagents and analytes to homogeneity is more difficult and time consuming in smaller reaction vessels, necessitating the need for some mechanical vibratory means, for example. Lilja reports that the optimal vibrational frequency and amplitude is best determined experimentally. Ultrasonic mixing has also been put forward by Liston (in U.S. Pat. No. 4,528,159), by Yang (Yang Z et al, 2001, Ultrasonic micromixer for microfluidic systems. Sensors Actuators A: Physical 3:266-272), and by Yaralioglu (Yaralioglu GG et al, 2004, Ultrasonic mixing in microfluidic channels using integrated transducers, Anal Chem 76:3694-98). Centrifugation has used for mechanical mixing and dissolution of reagents from reagent discs, as in the Piccolo Chemistry Analyzer (CardinalHealth, Dublin Ohio), which delivers results in about 12 minutes and is described by Schembri (Schembri CT et al, 1992, Portable simultaneous multiple analyte whole-blood analyzer for point-of-care testing, Clin Chem 38:1665-1670). Other mixing means are proposed in U.S. Pat. Nos. 6,382,827 and 6,808,304, and recently by Qian (Qian M et al, 2008, Fabrication of microfluidic reactions and mixing studies for luciferase detection. Anal Chem 80:6045-50), pointing to a difficult and unsolved problem.

Hammond, in U.S. Pat. No. 4,965,047, describes an analytical test strip with frangible blister to hold a diluent or reagent solution. A sample reacts with the liquid reagent in an absorbent layer and endpoint color is read by reflectance in a viewing window. Kitaguchi in U.S. Pat. No. 7,625,760 observes that uTAS methods which utilize reagents supplied from outside the chip where the analysis is performed are well known, such as early proposed by Wilding (U.S. Pat. No. 5,304,487). But noting that this level of complexity is not well suited for point of care analytical applications, Kitaguchi proposes methods for on-cartridge liquid reagent storage and release suitable for quantitative analysis. As observed for example in FIGS. 8 and 13 of the Kitaguchi patent, this method nonetheless adds substantial complexity to the device compositions and is apparently limited to endpoint assays because of the difficulty in instantaneously mixing reagents and analytes.

Subraminian in U.S. Pat. No. 5,223,219 relies on capillary flow and a porous reflective matrix to perform assays for a variety of clinical analytes in blood applied directly to the device. A monitor records the reflectance of the device reaction matrix during the assay reaction, typically at three wavelengths. By comparing the change in reflectance at an endpoint with those for known calibration materials, the monitor can compute the analyte concentration. However, capillary flow has proven difficult to standardize and the irregularities may increase overall assay reproducibility and accuracy.

Oosta in U.S. Pat. No. 5,478,751 describes devices made of self-venting materials in which a reaction such as the glucose oxidase/peroxidase assay for blood glucose is allowed to react to completion in a sample and then the intensity of an indicator dye is read spectrophotometrically. A device body made of microporous polypropylene films, monofilament woven screens, or other hydrophobic, air transmitting materials, is used to eliminate air from the internal channel.

Naka, in U.S. Pat. No. 6,001,307, claims a device for small scale analytical measurements in liquid samples. After the analytical reaction has proceeded for a selected period of time, any resulting pigment is entrapped in a filter paper or sponge in an optical viewing area and measured by densitometry, using reflected light for measuring the production of a pigment Immobilized solid state immunochemistries may also be deployed in the optical viewing area, where a sandwich of analyte and binding reagent is assayed after a defined reaction time. In other words, the assay methods are again limited to endpoint reactions. The inventors also stress the importance of a bypass channel (6) in the claims, which is used so as to take up excess sample or entrained air and neutralize any excess suction pressure (Col 14, lines 25-53, Col 4, lines 40-55), implementing by design diminishing flow resistances greatest in an upstream drawing channel segment, less in a bypass channel, and least in a downstream analytical channel, although this would seem unnecessary in practice.

Naka, in U.S. Pat. No. 6,325,975, further describes an elongate sampling channel affixed to a small thumb-sized suction chamber, the suction chamber having elasticity for generating suction when deformed and released, where the elongate channel contains a second chamber having a "sample analysis device" which contains immobilized reagents for reacting with an analyte. The device has the disadvantage that the sample must be admitted to the device after the suction chamber is depressed, there being no check valve or vent to prevent expulsion of the sample upon application of positive pressure. Also, the incorporation of reagents in a laminated membrane effectively limits reaction rates to diffusional kinetics which are independent of analyte concentration, thus limiting the device to endpoint reactions.

It can be desirable to have results from multiple assays in order to better characterize the clinical status of a patient. Test panels are most helpful if available in real time at the point of care. Challenging are multiple analyses to be performed on sample sizes of 10 or 20 microliters of whole blood, such as obtained with capillary sample tubes. Of particular difficulty are pediatric blood samples, where a high hematocrit is associated with reduced plasma volume of the sample.

Where multiple assays are desired from a minimum sample volume, it may be desirable to perform the assays in series rather than in parallel, metering out the sample only as needed, and in order to accomplish that, a means for separating plasma from whole blood "on demand" is needed, where sufficient plasma is drawn off for performing one reaction at a time so that as many assays as possible may be performed, in rank order of their clinical importance.

As has also been noted in the literature, elimination or reduction of diluent and reagent volumes results in an increase in sensitivity, but a satisfactory solution has not been presented for the problem of passively dispersing any inhomogeneities that occur during direct rehydration and mixing of dry reagents in a minimal sample liquid, where "passively" indicates an absence of mechanically assisted mixing.

In the case of kinetic assays, where a rate of a reaction under zero-order kinetic conditions is desired in order to measure the concentration of a selected analyte, what is needed is a device that can instantaneously mix a sample containing the rate-limiting analyte with all reactants and cofactors participating in the reaction and then, in a very short period of time during which the reaction rate is linear, before other reactants become rate limiting, measure a steady state reaction rate. This condition has not been met without use of a substantial sample or reagent volume taken up and manipulated in dedicated mixing circuitry powered by an external driver, for example as described by Lilja above, because without adequate mixing, the reaction rate is diffusion limited, not analyte limited, and therefore a rate or "kinetic" analysis cannot be achieved.

In view of the above, a need exists for a microfluidic device for conducting small-volume clinical assays by rapidly rehydrating and homogenizing dry reagents in a minimum of sample volume under passive mixing conditions, where the rate of reagent dissolution in sample is not so slow that analyte reaction kinetics cannot be measured. The present invention provides these and other features that will be apparent from the disclosure herein.

BRIEF SUMMARY

A microfluidic cartridge is described for performing one or more clinical assays in sub-microliter reaction chambers. Each reaction chamber is cut from an ACA layer laminated between two optically transparent films enclosing the chamber, the transparent films forming optical windows for transillumination of the sample. The sample is urged into the reaction chamber by application of a downstream suction pressure under stop flow conditions. No vent to atmosphere is provided on the cartridge. In the reaction chamber, a dehydrated chromogen in a dry reagent matrix is dissolved rapidly in the sample, triggering the start of the analytical reaction under conditions of substrate and cofactor excess. The dry reagent matrix is pre-printed in the reaction chamber during manufacture. In the assay, accumulation or disappearance of a reaction product such as NADH or a formazan is monitored spectrophotometrically through the optical windows. Convective eddy diffusion and molecular diffusion drive rapid dissolution of the reagents to optical homogeneity. Surprisingly, zero order kinetics for enzyme (or analyte) concentration are readily obtained by passive mixing despite the initial inconsistencies of chromogen dissolution in the reaction chamber, and spectrophotometric data sufficient for calculating enzyme concentration from the linear slope of accumulation of a reaction product may be collected in 5 to 60 seconds. No mechanical mixing is used.

The reaction chamber functions as a passive mixing device and a cuvette with a light path of less than 6 mils (about 150 micrometers) and a total volume of about 300 nL. The volume of the reaction is fixed by the stop flow barrier downstream, which is permeable to gas but not liquid.

Despite expected temporal variations in reagent dilution during rehydration, assay results are surprisingly consistent, and standard curves are readily obtained for rate reactions of clinical analytes over a clinically significant range of values. Initially, dissolution kinetics dominate and are a function of the rehydratable dry reagent matrix deposited on the optical window or windows in the reaction chamber. The rehydratable dry reagent matrix is configured for homogeneous dissolution under static conditions by passively-driven convective mass transfer operatively coupled to the filling of the fixed volume of the analytical arm with the fluid microsample in response to a suction pulse applied downstream. Absorbance is determined by a chromogen deposited in the reaction chamber, the selected chromogen having an absorbance at a defined wavelength or wavelengths specific for a reaction with the clinical analyte of interest in the analysis.

The assay reaction can be analyzed as having two phases, where mixing kinetics dominate the early dissolution phase, and zero order reaction kinetics dominate the analytical phase, and the two phases are essentially discrete because of the small fixed volume and rapid equilibration. The two phases can be observed by monitoring absorbance. An inflection point in the first derivative of absorbance separates the first phase and second phase of the analysis. During the second phase, reactants are in excess and any change in absorbance follows zero order kinetics for the analyte.

In this way, the homogeneous dissolution of the chromogen defines a first phase of the assay and the reaction of said chromogen with the clinical analyte defines a second phase of the assay. The first phase and the second phase are separated by a change in sign of the first derivative of the absorbance associated with the chromogen of interest. The second phase of said analysis is further defined by a change in absorbance that is zero order for the analyte. Under these conditions, the concentration of the analyte of interest may be measured in the sample.

The nature of the dried reagents pre-loaded on the cartridge determines what analyte will be assayed. For assay of blood enzymes for example, dehydrated enzyme substrate deposited in a microfluidic intake channel is dissolved in the sample when the sample is drawn into the reaction chamber. In the reaction chamber, an optically active cofactor initiates the reaction, which can be monitored by measuring absorbance. For assay of clinical substrates such as glucose, dehydrated enzymes and cofactors may be deposited in the intake channel between the sample receptacle and the reaction chamber and a chromogen indicative of the reaction is deposited in the reaction chamber.

Each cartridge may contain multiple assay subcircuits: each subcircuit consisting of a reaction chamber connected to a common sample receptacle by an upstream microfluidic intake channel and connected to a common downstream suction manifold and off-cartridge suction pressure source. A hydrophobic, gas-permeable barrier or capillary stop is placed downstream from the reaction chamber. When flow reaches the stop flow barrier, the flow is arrested and bulk turbulent mixing in the reaction chamber ceases. Advantageously and unexpectedly, diffusional and osmotic convective eddy mixing was found to be sufficient to achieve optical homogeneity within a few seconds.

Advantageously, stoppage of flow, which intuitively would seem to limit mixing, instead promotes static, steady state reaction conditions ideal for zero-order kinetic assays, and also conserves sample, so that multiple assays may be run from a single sample placed in common sample receptacle or well.

During rehydration, part of the reagent in the reaction chamber is likely to exit the chamber as the chamber is wetted, filled and flushed of air. Under conditions of static flow, absorbance drift is avoided, as was found to occur when a reagent was progressively washed out of the chamber by continuing flow past the fill volume of the reaction chamber. The reaction chamber and stop flow barrier establish a fixed volume that is accurately reproduced from cartridge to cartridge.

Whole blood, serum, plasma, urine or cerebrospinal fluid may be conveniently used in the cartridges of the invention. Since the rehydrating diluent volume is typically the biological sample itself, quantitative analyte data per unit volume is readily obtained. Reactant interferences are overcome through use of multi-wavelength analysis or by selective upstream adsorption. On-cartridge filtration of red blood cells through the use of in-line depth filter membranes is used to obtain hemolysis-free plasma as required. Assays that can be run on plasma include clinical chemistries such as electrolytes, serum enzymes, blood glucose and urea nitrogen, creatinine, hormones, and so forth. Most immunoassays may also be performed on plasma. Assays may be endpoint assays or rate assays.

In one embodiment, disclosed is a disposable microfluidic cartridge with on-board reagent or reagents for one or more micro-volume clinical assays. In another embodiment, disclosed is a combination of a microfluidic cartridge with multiple assay subcircuits, each with on-board dry reagents for analysis of a different analyte, and a host instrument or workstation for control of the reactions and for collection of data forming a panel of test results. Several assays may be run from a few microliters of plasma, or other sample. In another embodiment, a single cartridge may be used to assay multiple samples.

In another embodiment, where sample conservation is desired, assay reactions are run serially, one at a time from a common sample well. Two to ten microliters of blood plasma are thus sufficient to run a multiplicity of assays. Running one assay at a time ensures that very small differences between the flow resistance of one assay subcircuit and another does not result in inconsistencies in wetting times. Active spectrophotometric data sampling is continuous through the process of sample loading and analysis. Data to be used for rate calculation is chosen to match a period of steady state linear change in absorbance as optical density versus time.

BRIEF DESCRIPTION OF THE DRAWINGS

The teachings of the present invention can be readily understood by considering the following detailed description in conjunction with the accompanying drawings, in which.

DETAILED DESCRIPTION

Definitions

Certain meanings are defined here as intended by the inventors, i.e., they are intrinsic meanings. Other words and phrases used here take their meaning as consistent with usage as would be apparent to one skilled in the relevant arts.

Certain terms throughout the following description and claims are used to refer to particular features, steps or components. As one skilled in the art will appreciate, different persons may refer to the same feature, step or component by different names. This document does not intend to distinguish between components, steps or features that differ in name but not in function or action.

Certain features or components herein may be shown in somewhat schematic form and some details of conventional elements may not be shown in the interest of clarity and conciseness. The drawing figures are not necessarily to scale.

"Diffusion", as used herein, refers to the process whereby molecules move in a summation of random motions toward equilibrium between regions of higher concentration and regions of lower concentration.

"Convection", as used herein, refers to a process of eddy mixing involving the mass movement of parts of a fluid within the fluid because of differences in the density or temperature of the different parts.

"Convective mass transfer" refers to mass transfer taking place through both diffusion and by fluid motion in the form of eddies, in which matter is transported by the larger-scale motion of currents in the fluid, and thus describes transport by a combination of molecular diffusion and eddy mixing. Convective mass transfer is "passively driven" when not driven by mechanical energy applied to the system. When convention is driven by osmotic gradients, the energy for convective mass transfer is passively stored in the device as manufactured, and is a form of potential energy which is released on wetting.

"Chromagen" refers to a chemical or compound that reacts to produce a colored end-product, as is used in analytical chemistry and enzymology to detect the presence of an analyte of interest.

Absorption spectroscopy refers to spectroscopic techniques that measure the absorption of light, as a function of wavelength, due to its interaction with the molecules of a sample. The intensity of the absorption (or transmission) varies as a function of wavelength, and this variation is the absorption spectrum. Absorption spectroscopy is employed as an analytical chemistry tool to determine the presence of a particular analyte in a sample and, in many cases, to quantify the amount of the analyte present.

ACA layer: refers to a double sided adhesive material having three stacked layers, where two adhesive layers are separated by a central core or carrier layer such as the 8141 acrylic adhesive film (3M Company, St Louis Mo.).

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, particular features, structures, or characteristics of the invention may be combined in any suitable manner in one or more embodiments.

"Conventional"—refers to a term or method designating that which is known and commonly understood in the technology to which this invention relates.

Unless the context requires otherwise, throughout the specification and claims which follow, the word "comprise" and variations thereof, such as, "comprises" and "comprising" are to be construed in an open, inclusive sense, that is as "including, but not limited to".

The appended claims are not to be interpreted as including means-plus-function limitations, unless such a limitation is explicitly recited in a given claim using the phrase "means for."

Although the following detailed description contains specific details for the purposes of illustration, one of skill in the art will appreciate that many variations and alterations to the following details are within the scope of the invention. Accordingly, the particular embodiments described below by way of teachings are set forth without any loss of generality to, and without imposing limitations upon, the claimed invention.

Figure 1A:
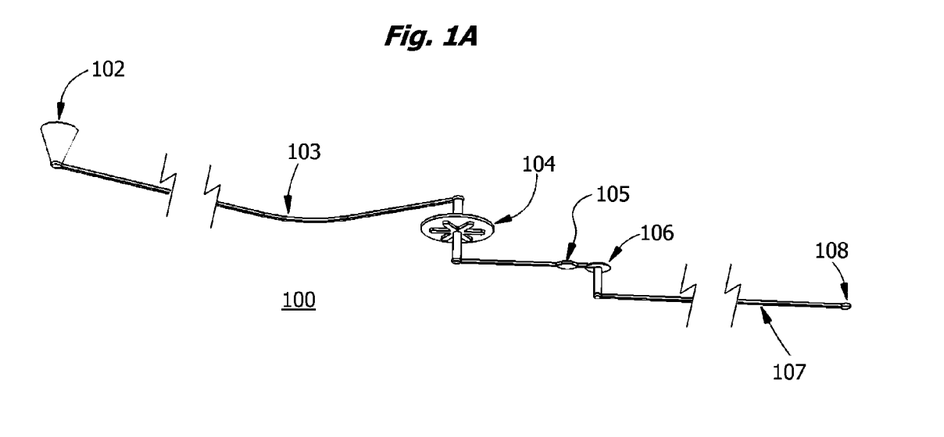
FIGS. 1A and 1B are worm's eye views of a single-channel analytical subcircuit.

Turning now to the figures, FIG. 1A depicts a schematic view of one embodiment of a basic microfluidic "subcircuit" or "assay circuit arm" 100 of the invention. The view is looking up from beneath the cartridge body containing the circuit. The body of the cartridge is not shown. In use, a whole blood sample, for example, is introduced into the circuit in sample receptacle 102. On command of a host workstation, sample then is pulled through a depth filter 104, and into the reaction chamber 105. The length of an upstream intake channel 103, which connects the sample receptacle to the reaction chamber 105, may have a length as reasonably required for layout on the cartridge body. A downstream outlet channel 107 connects the reaction chamber to an actuation port 108 or valved connection to an off-cartridge suction manifold, such as a syringe pump or buffered vacuum reservoir. Between the reaction chamber 105 and the downstream actuation port 108 is a hydrophobic, gas permeable membrane or a capillary stop 106 for arresting flow of the sample once the reaction chamber is full. Hydrophobic, gas permeable, liquid impermeable membranes function as a "stop flow barrier". Capillary stops also function as stop flow barriers and may be used interchangeably. The reaction chamber is provided with upper and lower optical windows and is configured to interface with a docking bay and a spectrophotometer of a host workstation. The docking bay is optionally temperature controlled; the spectrophotometer may comprise an LED and photodiode pair, for example, for transilluminating the reaction chamber and measuring absorbance of a substance therein.

Figure 1B:
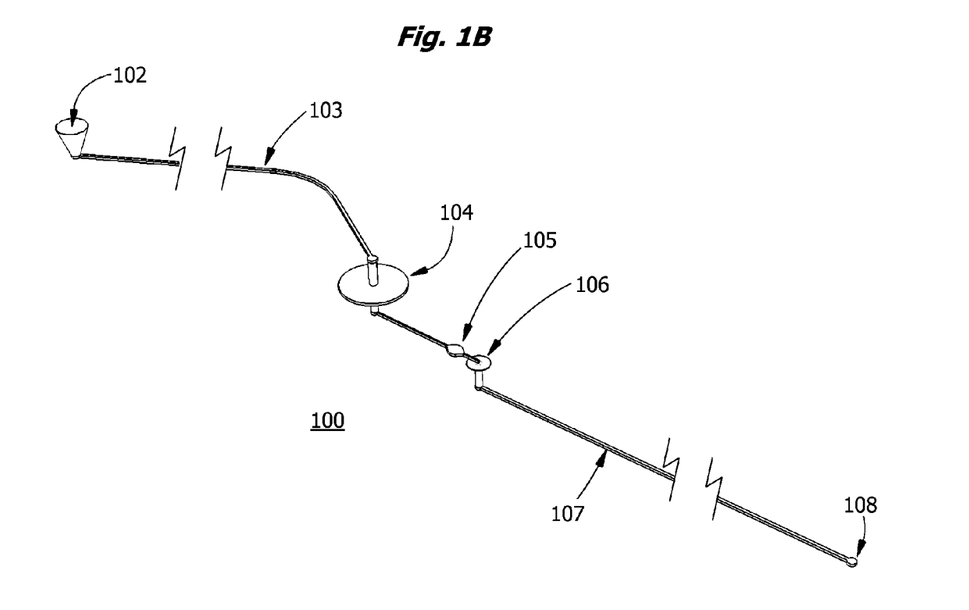

This basic microfluidic circuit is shown again in FIG. 1B from a view looking down. Fluid sample is deposited in sample receptacle 101. On command of the host workstation, fluid then is admitted via upstream intake channel 103 into the reaction chamber 105, generally by generation of a suction pressure at port 108. The reaction chamber is then transilluminated and interrogated spectrophotometrically through the opposing paired optical windows forming the top and bottom surfaces of the chamber. The walls of the reaction chamber are cut from an ACA layer used to laminate together the film layers forming the optical windows. Dry reagents printed in the fluid channels dissolve and react with an analyte in the sample. Fluid flow is stopped at stop flow barrier 106 in downstream fluidic channel 107 during data collection. A chromogen printed in a dry reagent matrix on an optical window dissolves rapidly after static no flow conditions are achieved. Thus a finite volume of sample is used in each assay and reagent concentrations are reproducible. Typically the fixed volume defined by the reaction chamber and the stop flow barrier is about 400 nL or less.

Dry reagents deposited during assembly of the cartridge in upstream fluidic channel 103 and in reaction chamber 104 are dissolved in the sample, not in a buffer or intermediate solution. The optically active chromogen needed to monitor the assay is placed in the reaction chamber where its absorbance can be actively monitored during a first phase and a second phase, the first phase corresponding to the dissolution phase and the second phase to the analysis or "rate kinetics" phase of the assay.

Figure 2A:
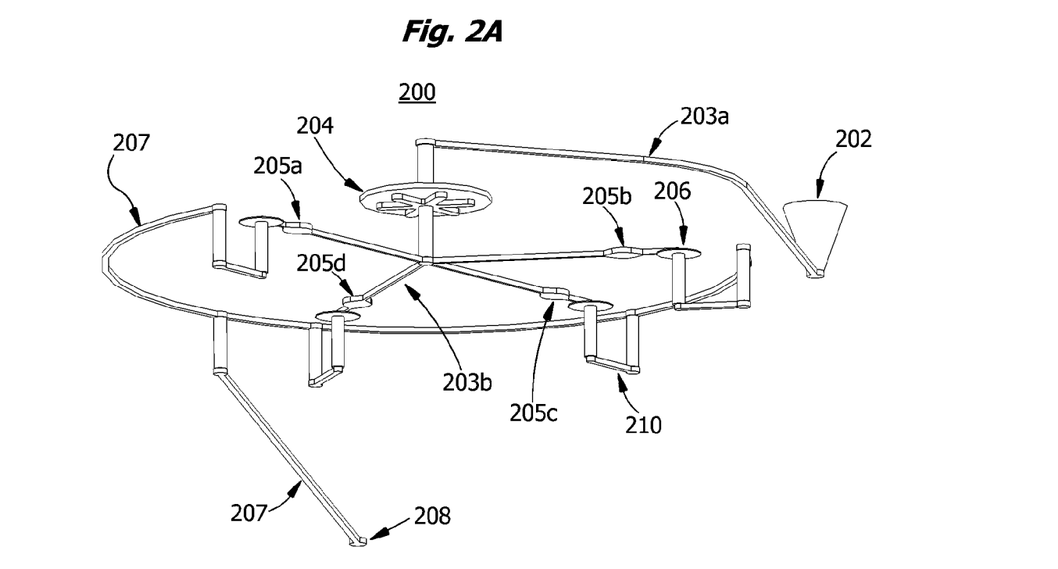
FIGS. 2A and 2B are worm's eye views of a multiple channel analytical subcircuit.

FIG. 2A depicts a more complex cartridge with multiple parallel pathways for up to four assays. Sample receptacle 202 is fluidly connected by intake channel 203a to a depth filter 204 for separating red cells from plasma, but the intake pathway then splits into four branches (203b), each with a separate reaction chamber 204 and stop flow barrier 206. Indicated clockwise around the circle are first reaction chamber 205a, second reaction chamber 206b, third reaction chamber 205c, and fourth reaction chamber 205d. The reaction chambers are joined by a common downstream outlet channel 207, here with a constant radius around the central depth filter via, and terminal segment ending in actuation port 208, which is fluidly connected to an off-cartridge pressure differential for pulling sample flow through the depth filter and into the reaction chambers when the cartridge is docked in the host workstation and the assay is initiated.

Stop flow barrier 206 seats on "U-channel" 210. In a certain embodiment, all channels are operated in parallel by applying suction pressure in unison to each of the branches dissecting from the sample receptacle. While small differences in flow resistance between each branch may exist, as each channel is filled and flow is stopped at each of the stop flow barriers 206, the remaining channels also will fill.

Figure 2B:
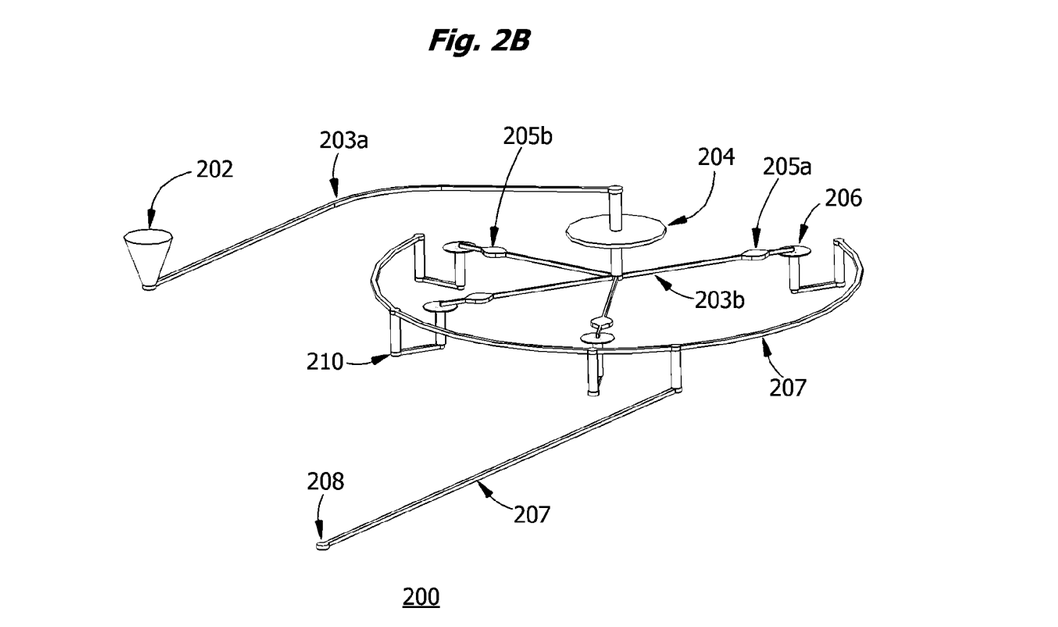
Figure 3:
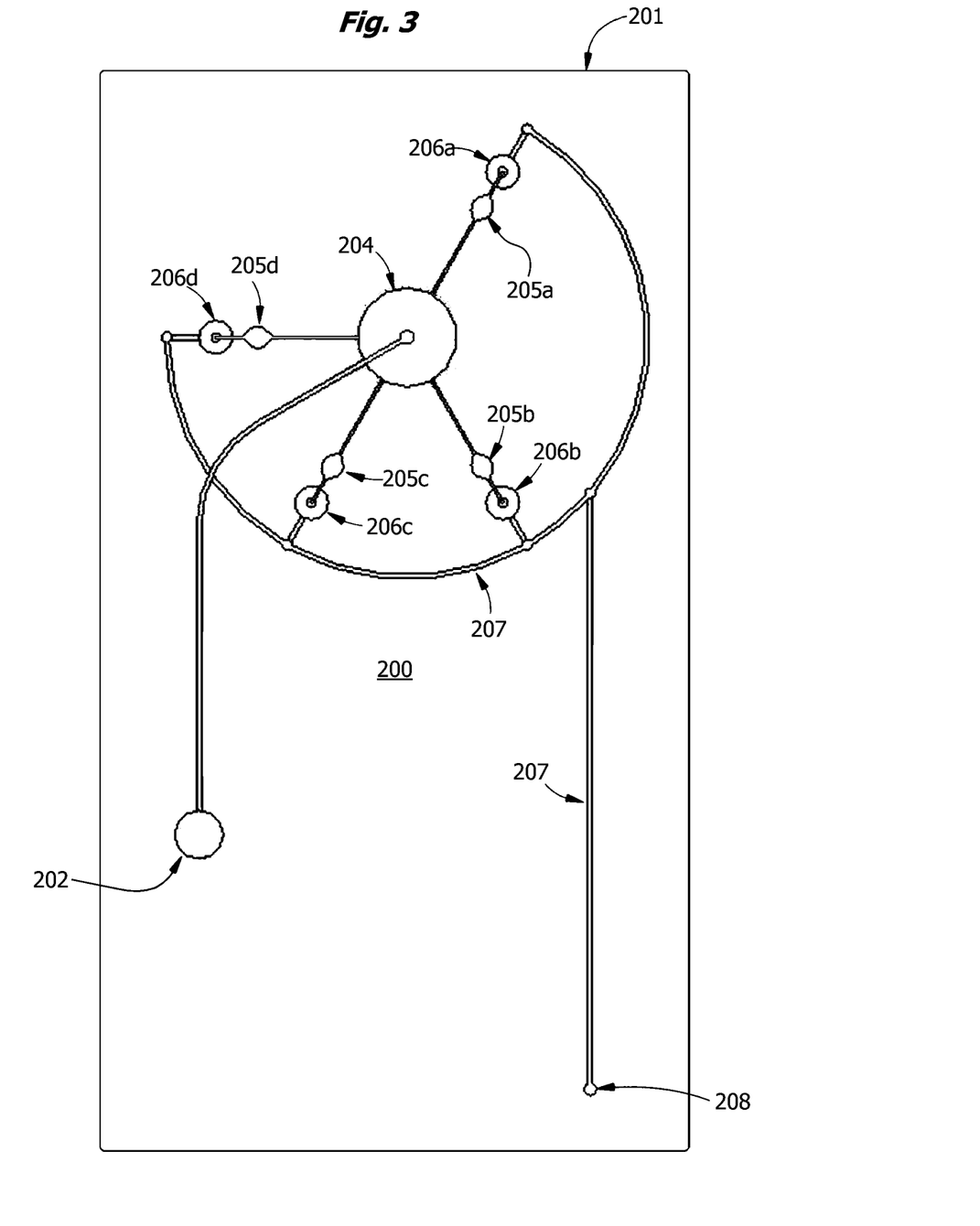
FIG. 3 is a plan view of a microfluidic cartridge with off-cartridge pneumatic interface for controlling multichannel cartridge-based liquid processes.

FIG. 3 schematically illustrates the four-armed microfluidic circuit 200 and cartridge body 201 of FIG. 2 in plan view. The cartridge body is typically configured to seat in a temperature-controlled docking bay of a host instrument and pneumatically engage a suction pressure manifold at actuation port 208. The user first fills sample receptacle 202 with a liquid sample and then starts the assay. The cartridge has the shape of a playing cartridge in this illustration, and may be a few millimeters thick.

The multi-assay cartridge 201 of FIG. 3 contains four assay sub-circuits in a single plastic body 201. In this plan view, the sample reservoir 202 is fluidic connected with a filtration unit 204 in the center of four reaction chambers 205a, 205b, 205c and 205d, each with associated stop flow barriers 206a, 206b, 206c and 206d and joining channels. Microfluidic channels join each reaction chamber to the sample receptacle 202 at the central hub and to downstream actuation port 208 by a common downstream channel 207 disposed circumferentially like the rim of a wheel around the central hub with assay arms projecting as spokes therebetween. The downstream channel 207 is fluidly connected to a vacuum source on the host workstation (not shown) via port 208, which may be valved on card or valved remotely on the workstation.

As shown, all valves and downstream channels except common suction manifold 207 and actuation port 208 are eliminated so that the architecture of the cartridge may be simplified. All subcircuit assay arms are actuated in parallel and simultaneous data is collected from each reaction chamber.

Optionally each arm of the suction manifold is separately valved and controlled. In alternate embodiments, the valves are pneumatically actuated via a pneumatic manifold under control of the host instrument, and are actuated one at a time. The control pneumatic ports are aligned on the edge of the cartridge so as to sealedly interface with the docking adaptor of the host workstation. Port 208 is joined to the circular downstream channel 207, which forms a common suction manifold. Separate control ports for the independent valves are formed at the interface between card and host instrument. Alternatively, each assay circuit arm is connected to an independent port for off-cartridge suction pulse.

Figure 4A:
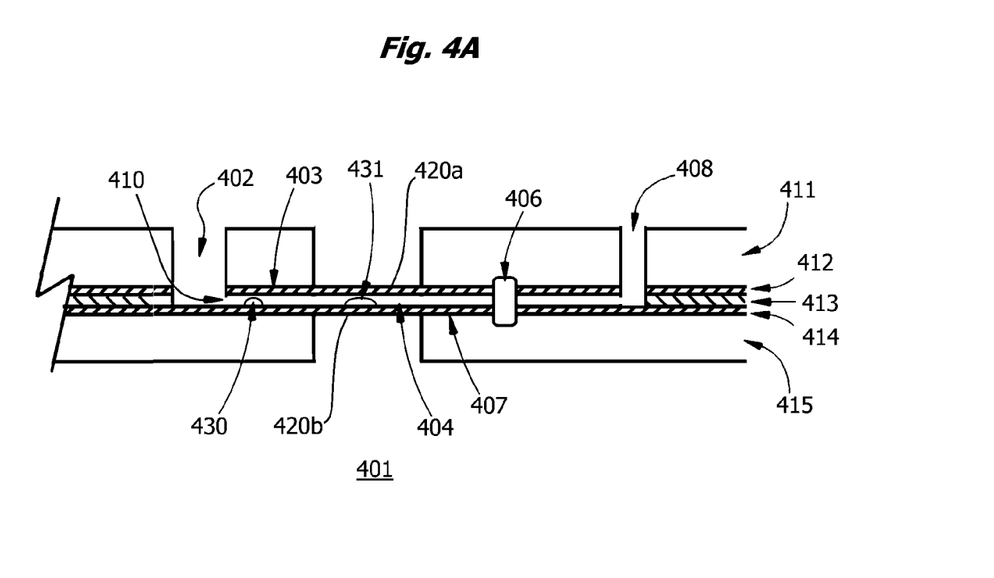
FIGS. 4A and 4B are, respectively, plan and long axis cross-sectional view of an analytical subcircuit for analyzing a liquid sample not requiring on-cartridge filtration.

As shown in FIG. 4A, a cartridge body 401 of the invention may comprise multiple layers, for example, and may be assembled by lamination. Members 411 and 415 comprise the top and bottom members of the cartridge. Layers 412 and 414 form the upper and lower optical windows (420*a*, 420*b*) of the reaction chamber and are fabricated of transparent plastic. Layer 413 forming the walls of sample receptacle 402, intake channel 403 and outlet channel 407 is a double layered adhesive layer (ACA layer). Stop flow barrier 406 is shown figuratively, and may be a hydrophobic gas-permeable insert. Optionally, stop flow barrier 406 instead may be a capillary stop. Layers 412 and 414 may be joined to body layers 411 and 415 by solvent welding, by ultrasonic welding, by diffusion, by gluing, or by additional laminated ACA layers. The cartridges may be fabricated by lamination, molding or by a combination of lamination and molding by methods known in the art. Experience has shown that the optical windows are advantageously formed of a cyclic olefin copolymer film such as Zeonor® film (Zeon Chemical, Louisville Ky.) or Topaz® 8007F-400 (Ticona, Florence Ky.), a cyclic polyolefin plastic with improved light transparency from 275 to 800 nm.

For illustration, the device is shown to contain two dried reagent spots, 430 and 431. Reagent spot 430 may contain a substrate, substrates, enzyme or enzymes, and is rehydrated and mixed with the sample prior to sample entry into the reaction chamber. Reagent spot 431 contains a chromogen that will be wetted and dissolved in a fixed volume defined by the volume of reaction chamber and stop flow barrier, where liquid flow is stopped. Both dried reagent spots are rehydratable in the liquid microsample and contain lyoprotectants and plasticizers to ensure activity is preserved during dessication and storage. The spots may also contain a binder for quicker wetting and dissolution. A variety of lyoprotectants in addition to sucrose or trehalose may be used. These include arabinose, erythritol, fructose, galactose, glucose, lactose, maltitol, maltose, maltotriose, mannitol, mannobiose, mannose, ribose, sorbitol, saccharose, xylitol, xylose, dextran, or mixtures thereof A plasticizer may also be used to control the melting temperature of the amorphous glass phase. Plasticizers include glycerol, dimethylsulfoxide, lower molecular weight polyethylene glycol, propylene glycol, diethylene glycol dimethylether, triethyleneglycol dimethyl ether, tetraethylene glycol dimethyl ether, N,N-dimethylacetamide, N,N-dimethylformamide, tetramethyurea, water, or mixtures thereof Plasticizers can also be useful in controlling the degree of crystallinity of the solid phase. Binders are also used to control rehydration kinetics and for powder handling. Binders include polyvinylpyrrolidinone, polyvinylpyrrolidinone, high molecular weight polyethylene glycol, a block copolymer of polypropyleneglycol and polyethylene glycol, polyacrylate, polymethylmethacrylate, poly-(d-1-lactide-co-glycolide), triethylene glycol dimethylether, butyl diglyme, chitosan, a cellulose, a methylcellulose, an alginate, an albumin, a dextran, a starch, a gelatin, a surfactant, or mixtures thereof Multiple reagent spots may be employed if needed, and configured for the requirements of particular assays. The rehydratable dry reagent matrix optionally comprises a buffer salt and a lyoprotective agent, and said rehydratable dry reagent matrix is printed as a liquid precursor on an inside surface of said optical windows and dried in place, so that passively-driven convective mass transfer is driven by the osmotic potential of the buffer salt and the lyoprotective agent, ensuring a rapid dissolution phase.

Figure 4B:
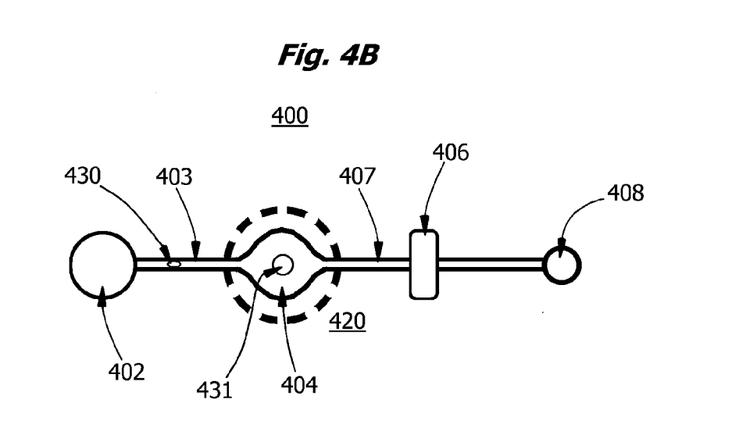

In this example, a liquid microsample such as plasma, serum, urine, or cerebrospinal fluid is shown entering the microfluidic circuit at 410 when suction is applied at actuation port 408. A simplified cartridge with microfluidic subcircuit 400 is shown in plan view in FIG. 4B. To perform an assay, the first step is to introduce a sample into sample receptacle 402. The assay is then actuated by a suction pulse received through actuation port 408, which causes sample fluid to flow into intake channel 403. Any reaction substrate deposited in a dry reagent matrix in the channel is rehydrated and carried along with the sample, which enters reaction chamber 404 under optical viewing window 420. The reaction is started by dissolution of a reagent or cofactor deposited in a dry matrix in the reaction chamber. The sample ceases to flow when it contacts stop flow barrier 406 and the reaction rapidly reaches steady state kinetics. Reactants become homogeneous in a matter of seconds due to osmotic eddy convection and diffusion. Absorbance data is collected through optical windows 420. Transmission spectroscopy is the preferred method of collecting data, although other instrumental modalities may be used. The host instrument is equipped with an LED, collimating lens, any filters, and a photodiode with high gain amplifier for detection of absorbance in the optical viewing chamber, which is essentially a miniature cuvette with a light path length of about 150 micrometers. The host workstation also is responsible for processing the data and for any on-board curve fitting; although optionally an analog-to-digital converter and dataport may be used so that data processing functions can be performed by a remote computer digitally yoked to the host workstation.

The host workstation may be, for example, a microFlow™ System (Micronics, Redmond Wash.), an integrated microfluidics workstation featuring low-pulse twist syringe pumps. Micronics' twist syringe pumps allow flow rates of 1-10,000 nanoliters per second. The workstation uses programmable software for directing on-cartridge reactions. The workstation is fitted with a pneumatic umbilicus and sealable adaptor for edgewise docking microfluidic cartridges such as that shown in FIG. 3.

Each cartridge typically contains only one sample reservoir 402. However, multiple assay subcircuits or "arms" are optionally connected to the single reservoir. Each subcircuit connects with a separate optical viewing chamber 404 radially arrayed around the sample reservoir 402 like spokes on a wheel, such as are illustrated in FIGS. 2 and 3. Optionally, an endpoint assay may also be performed; sample and reagent blanks may be measured in an adjoining arm or arms of a multi-armed device. In other embodiments, multiple wavelengths are measured through each optical window. Optionally, a single cartridge may contain multiple sample reservoirs and microfluidic analysis circuitry.

In one embodiment, each assay subcircuit is actuated one at a time. Only enough sample to fill the sub-circuit to the capillary stop 406 is dispensed per reaction, essentially the sample is dispensed "on demand" into each reaction channel. The identity and nature of the dry reagents in the reaction arm determine the assay to be run by that subcircuit. When one reaction is complete, which may take about 120 seconds or less, a second assay may be started. Because each assay requires less than a few hundred nanoliters of sample, multiple assays are performed from a 10 or 20 microliter sample receptacle. In another embodiment, all the arms of the device are actuated in parallel and sample is drawn into each arm simultaneously so that multiplex data can be collected.

Figure 5A:
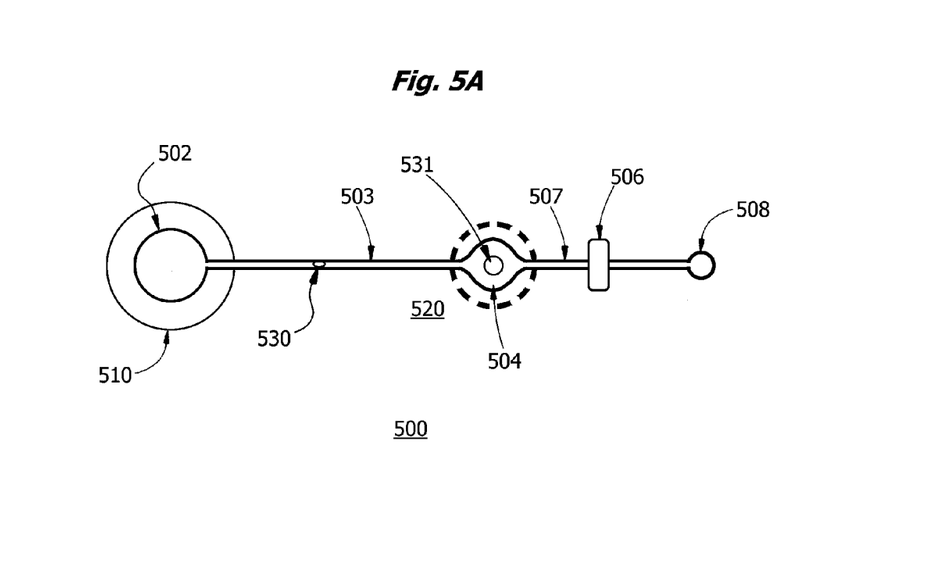
FIGS. 5A and 5B are, respectively, plan and long axis cross-sectional view of an analytical subcircuit for analyzing a liquid sample requiring on-cartridge filtration.
Figure 5B:
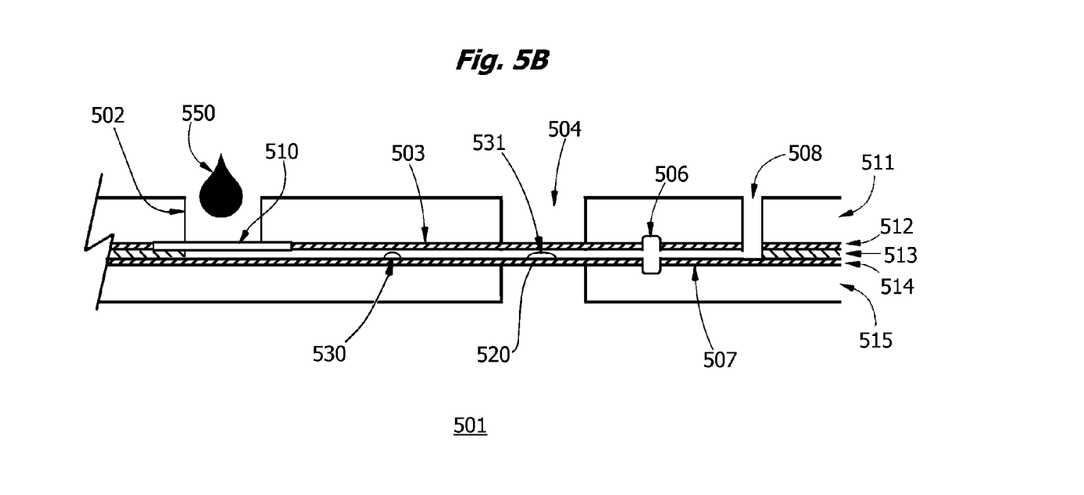

FIGS. 5A and 5B depict a plan and cross-sectional view of another embodiment of a microfluidic subcircuit 500 of the invention. Here the cartridge includes a membrane 510, such as a polysulfone depth membrane (for example the BTS-Vivid GF, Pall Corp, East Hills, N.Y.) for micro-filtration of whole blood and collection of plasma. Blood 550 is introduced into the circuit in whole blood receptacle 502 and passed through filter membrane 510. On command of the host workstation, a fraction of the plasma sample is pulled into the reaction chamber 504. Plasma may be filtered "on demand" from blood wetted in depth filter 510. An upstream fluidic channel 503 connects the reaction chamber to the sample receptacle. A downstream fluidic channel 507 connects the reaction chamber 504 to an actuation port 508 for valved connection to a downstream suction manifold, such as a syringe pump or buffered vacuum reservoir. Between the reaction chamber 504 and the downstream actuation port 508 is a stop flow barrier 308 for arresting flow of the sample once the viewing chamber is full. The device body 501 is mounted in a host instrument and optical absorbance data is collected by transillumination through viewing window 520.

The cartridge of FIG. 5B comprises five layers, while not limited thereto. Members 511 and 515 comprise the top and bottom members of the cartridge. Layers 512 and 514 form the optical windows 520 and are fabricated of optically transparent plastic. Layer 513 forming the walls of fluidic channels and chambers 503, 504 and 507 is a double layered adhesive layer (ACA layer). Cartridges of this sort may be fabricated by lamination, molding or by a combination of lamination and molding by methods known in the art and are made of materials such as polyethylene terephthalate (PET), polyacrylate, polystyrene, polycarbonate, polyamide, polyethylene or polypropylene, while not limited thereto.

Internal cartridge surfaces are optionally passivated if desired, and it has been found that selected treatments will result in increased dissolution and reaction rates, presumably by reducing passive binding of analyte or reagents.

Dry matrix materials such as polyvinylpyrrolidone (PVP) and trehalose are used to formulate reagents that are both stable in dry form on cartridge and rapidly dissolving. Substrates, buffers and reaction cofactors are dissolved in a liquid matrix precursor or precursors, which is or are spotted and dried or lyophilized in place on the cartridges. Optionally the cartridges may be stored in anhydrous foil pouches to increase shelf life. Frozen storage conditions may be used. A dry argon atmosphere in the storage pouch is also envisaged for difficult to store cofactors such as nicotinamide adenine dinucleotide (NAD), nicotinamide adenine dinucleotide phosphate (NADP), or flavin adenine dinucleotide (FAD), adenosine triphosphate, and so forth.

In this illustration, two dry reagent spots are shown. Optionally, more than or fewer than two reagent spots may be used. However, a spot 531 containing a chromogen to be monitored in the reaction is supplied in a rehydratable dry reagent matrix in the reaction chamber 504 of the device and is printed on one of the windows 520 where it is rapidly dissolved when wetted by a fluid microsample. Spot 530 shown here illustrates the provision of reagent spots in the entry channel 503 for delivery of reaction substrates, enzymes or other cofactors required in the assay.

Reagent dry matrix excipients including sugar and surfactant are designed to permit smooth even drying of the spotted reagent as well as fast, even rehydration when the assay is performed. A commercial-grade reagent spotter (Biodot) is conveniently used for manufacturing. Spotting volumes are generally on the order of 100 nl and dry to a few tens to a few hundreds of nanomoles of material. When wetted, osmotically driven diffusional and eddy mixing drive the dry mass to optically homogeneous solution in a matter of seconds. Final reactant mixture concentrations are in the range of a few mOs to less than a thousand mOs, preferably between 300 and 500 mOs for blood based assays.

Microfluidic cartridges of the invention may be used to analyze blood chemistries, including glucose, alkaline phosphatase, lactate dehydrogenase (LDH), aspartate transaminase (AST), alanine transaminase (ALT), creatine phosphokinase (CPK), lipase, cholesterol, triglycerides, uric acid, urea (BUN), creatinine, calcium, sodium, potassium, chloride, carbon dioxide, phosphorus, magnesium, iron, hemoglobin, bilirubin, creatinine, total protein, and so forth. Solid state immobilized immunoassay chemistries may also be performed using the optical wells of the invention.

Microfluidic conditions are notorious for the difficulty of obtaining turbulent mixing conditions and rates of diffusion are known to be limited by the molecular weight of the reactant. In the case of kinetic assays as assayed by transmission spectroscopy, linearity of reaction slope is not achieved until the reactants are in solution and homogeneously disposed in the light path. What is needed is a device that can essentially instantaneously mix a sample containing the rate-limiting analyte with all reactants and cofactors participating in the reaction in a reaction well under static flow conditions, and then, in a very short period of time during which the reaction rate is linear, before other reactants become rate limiting, measure a steady state reaction rate of the rate-limiting analyte. Generally, the window for data collection is no more than 120 seconds, more typically less than 60 seconds, so it is desirable that reaction steady state be rapidly achieved. Apparent steady state is lost when key reagents are exhausted or when reactant products accumulate in excess, such as when a chromogen exceeds its range for Beer's Law absorbance.

Generally, attempts to solve this problem using mechanical mixing aids were unsuccessful at this reaction scale. Because the solution volume is constrained by the stop flow barrier immediately downstream from the reaction chamber, and because of the need for near instantaneous data collection, mechanical mixing was abandoned as an option. This problem has been addressed by adding a dry chromogen spot (431, 531) directly on the windows of the reaction chamber, so that liquid sample that is static in the reaction chamber is mixed by eddy convection and diffusional mixing during rehydration of the dry reagent spot. Selected reagents may be placed in the upstream intake channel, and advantageously dissolved in sample therein, but at least one reagent, generally the chromogen to be optically monitored, is placed in the reaction chamber for this purpose. Then, given the small volume of the assay mixture, diffusional mixing when combined with eddy mixing is sufficient to rapidly resolve the dissolution phase and transition to analytical phase conditions where useful kinetic rate data may be collected.

The optical windows of the reaction chamber cuvette are advantageously formed of a cyclic olefin copolymer film laminated to form the ceiling and floor of the reaction chamber. Surprisingly, it has been found that the optical quality of the windows (120,220, 420, 520) enclosing the upper and lower surfaces of the reaction chamber are not degraded by the deposition of a range of matrix materials, including buffer, salts, reagent cofactors and enzymes, directly on the window portals. Dissolution is sufficient and complete so that essentially no degradation of optical transparency in the range of 275 to 800 nm or increase in scatter is apparent, achieving precision in kinetic rate assays in nanoliter volumes and an optical quality more than sufficient for most colorimetric and ultraviolet-based spectrophotometric assays.

EXAMPLES

Example 1

Lactate Dehydrogenase

Plasma LDH, which is elevated in liver disease and myocardial infarction, was assayed on a microfluidic cartridge essentially that of FIG. 5. To prepare the cartridge, an excess of sodium pyruvate in a PVP (K-12) and trehalose dry matrix was spotted in the upstream intake channel 503 and an excess of NADH as a dry matrix formulation in PVP-40 and trehalose with TRIS buffer (about 140 nmole/spot) was spotted in the reaction chamber 504 on optical windows 520.

For assay of LDH, upon application of a suction pulse at activation port 508, plasma from sample receptacle 502 was drawn through depth filter 510 and caused to rapidly fill the reaction chamber 504. The plasma volume used was limited by capillary stop 506. For collection of absorbance data, the cartridge was docked in a host apparatus or workstation (not shown). The workstation was programmed to collect spectrophotometric data at 340 nm continuously and the data was transferred electronically to a curve fitting program for calculation of LDH activity. Data for analysis is selected by an algorithm that finds the linear portion of the data. Representative data for an LDH activity of 2500 U/L is reported in FIG. 6. Decreases in $OD_{340}$ represent the oxidation of NADH.

Figure 6:
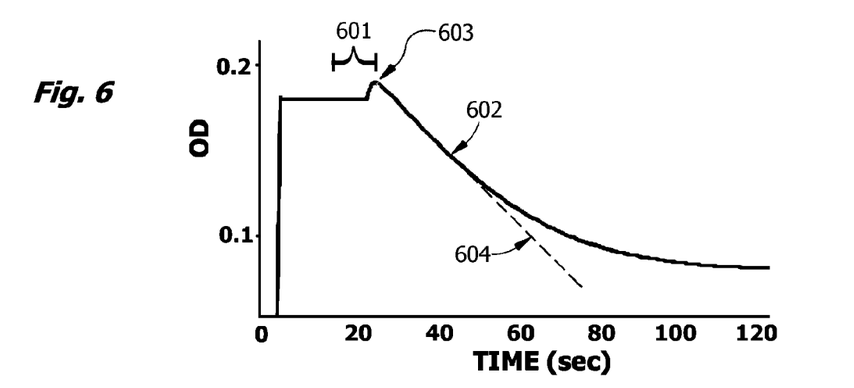
FIG. 6 is a curve fit showing linear reaction kinetics of a lactate dehydrogenase assay acquired with a microfluidic cartridge of the invention having reproducible rapid molecular and eddy diffusional mixing of dry reagents.

FIG. 6 illustrates the two phase aspect of the assay. In a first phase, termed herein the "dissolution phase" (601), a peak of NADH absorbance is observed. This peak is sharp and represents the rapid dissolution of the chromogen, here enzyme cofactor NADH, spotted in the reaction chamber. In a second phase, termed here the "analytical phase" (602), a steady decrease in absorbance is observed, characteristic of zero-order kinetics for enzyme concentration. Separating the two phases is a sharp inflection in the curve that can be monitored as a change in sign of the first derivative, and is thus compatible with machine analysis, permitting closed loop control of the assay. Absorbance following the flip in the first derivative can be analyzed with a linear curve fit (604, extrapolated as dotted line), and the analysis discontinued when the measured absorbance drifts away from the best linear extrapolation of the initial steady state rate. Thus the start point and the end point of the data acquisition cycle may be determined In practice, dissolution was found to be achieved in a few seconds, and analysis curve fits were completed in 15 to 90 seconds following that, depending on the analyte concentration.

Figure 7:
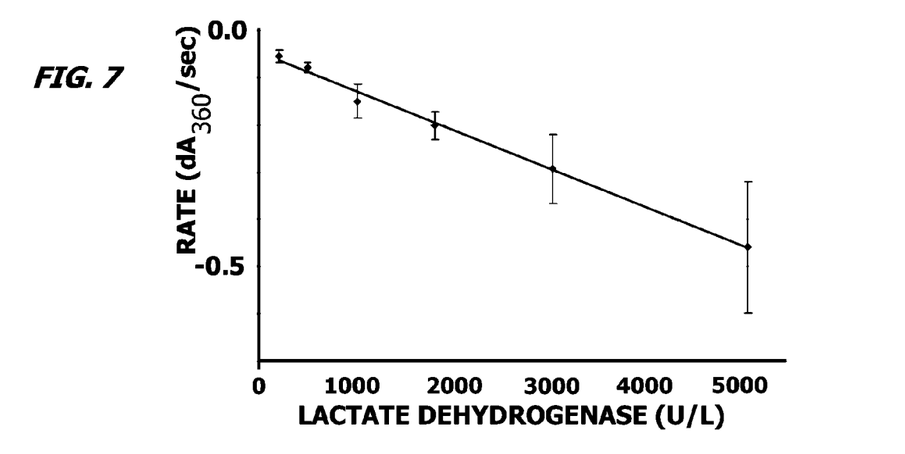
FIG. 7 is a standard curve for a lactate dehydrogenase assay performed with the microfluidic cartridge of a first embodiment of the invention.

A dynamic range for LDH of 500 to 5000 IU was achieved. A standard curve for LDH activity in the cartridges of the invention is shown in FIG. 7.

Optionally, LDH may be assayed by coupling with diaphorase, using the colored dye formazan as an indicator. Diaphorase is spotted in an upstream arm of the assay circuit arm and a formazan is spotted in the reaction chamber.

Reagent spotting may be performed during the cartridge manufacturing process using a commercial-grade reagent spotter (Biodot). Roll-to-roll manufacture with on-line reagent spotting is also conceived. Spotting volumes are generally on the order of 100 nl. The state of NADH in the gel-like dry reagent matrix remains largely intact. Matrix formulations for pyruvate and for NADH were optimized separately. Reagents were found to be stable when stored in foil vapor barrier bags at 4 C for extended periods of time. Kits containing cartridges for a variety of assays may be sold separately.

Example 2

Hemoglobin

Figure 8:
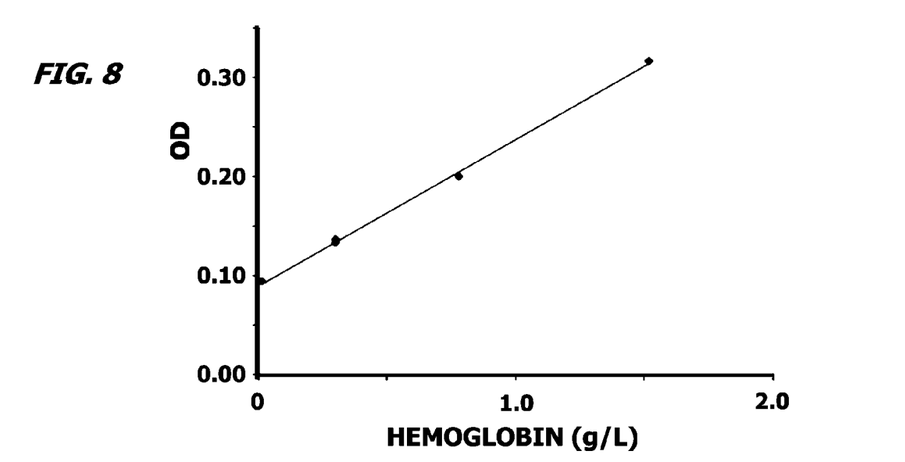
FIG. 8 is a standard curve for a hemoglobin spectrophotometric endpoint assay run with the microfluidic cartridge of a first embodiment of the invention.

Using the cartridge and apparatus of Example 1, filtered plasma was examined for free hemoglobin. Reagents were not used; plasma was instead optically interrogated at 415 nm and the data was used for rejecting LDH data from hemolyzed plasma specimens. Optionally, a multi-wavelength hemoglobin assay may be used to accurately quantitate free—or total lysate hemoglobin. A standard curve for free hemoglobin in plasma is shown in FIG. 8.

Example 3

Magnesium

Plasma magnesium was measured with isocitrate dehydrogenase and NADP+, using potassium citrate as the substrate and EDTA/glycol ether diamine N,N,N,N-tetraacetic acid as chelators. The method is based on that described by Sunahara in U.S. Pat. No. 5,108,905 with annotations by Stone (1996. Validation of an enzymatic total magnesium determination based on activation of modified isocitrate dehydrogenase. Clin Chem 42:1474-77).

Example 4

Glucose

Plasma glucose is measured with glucose oxidase. An excess of glucose oxidase and 3-methyl-2-benzothiazolinone hydrazone are dehydrated in spots in the intake channel 503 upstream from the reaction chamber. Horseradish peroxidase enzyme is spotted in the reaction chamber 504. All spots are dried and the cartridges are stored under argon until use. Upon application of a suction pulse at activation port 508, plasma from sample receptacle 502 is filtered through depth filter 510 and caused to rapidly enter and fill the optical viewing chamber. The plasma volume used was limited by stop flow barrier 506. An external workstation is programmed to collect rate data at 600 nm.

An endpoint assay is also feasible. A variety of dyes used in the assay of peroxide are described in U.S. Pat. No. 5,518, 891. Dyes resistant to bilirubin interference are reported in U.S. Pat. No. 5,792,619. Alternatively, the endpoint may be monitored fluorometrically by use of a fluorochrome such as Amplex® Red (Molecular Probes, Eugene Oreg.) (10-acetyl-3,7-dihydroxyphenoxazine, reduced form) and by substituting epifluorescence in the instrumentation package. Alternatively, endpoints may be measured using chemiluminescence or electrochemically or concentration data may be measured under conditions for zero-order rate of reaction for glucose.

All of the U.S. patents, U.S. patent application publications, U.S. patent applications, foreign patents, foreign patent applications and non-patent publications referred to in this specification and/or cited in accompanying submissions, are incorporated herein by reference, in their entirety. When cited works are incorporated by reference, any meaning or definition of a word in the reference that conflicts with or narrows the meaning as used here shall be considered idiosyncratic to said reference and shall not supersede the meaning of the word as used in the disclosure herein.

While the above is a description of certain embodiments of the present invention, it is possible to use various alternatives, modifications and equivalents. Therefore, the scope of the present invention should be determined not with reference to the above description but should, instead, be determined with reference to the appended claims, along with their full scope of equivalents.

In the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the specifics of the disclosure.

What is claimed is:

1. A microfluidic cartridge for performing an assay of a fluid microsample to detect a clinical analyte or analytes therein, the microfluidic cartridge comprising:
   a cartridge body, a sample receptacle for receiving said fluid microsample, and at least one assay circuit arm,
   said assay circuit arm comprising:
   a) an intake fluidic channel joining said sample receptacle to a reaction chamber, wherein said reaction chamber is enclosed by a gas permeable, liquid impermeable stop-flow barrier and opposingly paired optical windows, said optical windows for transilluminating said reaction chamber at a defined wavelength or wavelengths by an optical interface of a host workstation when said cartridge body is docked therein;
   b) a downstream fluidic channel joining said reaction chamber to an actuation port configured to receive a suction pulse, said downstream fluidic channel further comprising said stop-flow barrier interposed between said reaction chamber and said actuation port, said reaction chamber and stop-flow barrier defining a fixed wettable volume within said assay circuit arm;
   c) a dry reagent matrix deposited on one or both of said opposingly paired optical windows in said reaction chamber, wherein said dry reagent matrix is configured to enable homogeneous dissolution operatively coupled to the filling of said fixed volume with said fluid microsample in response to said suction pulse; and
   d) a chromogen deposited in said rehydratable dry reagent matrix, said chromogen having an absorbance at a defined wavelength or wavelengths specific for a reaction with said clinical analyte.

2. The microfluidic cartridge of claim 1, wherein said opposing paired optical windows are formed of two laminated layers of a cyclic olefin copolymer film separated by an ACA layer.

3. The microfluidic cartridge of claim 1, wherein said homogenous dissolution in said fixed volume is driven passively by convective mass transfer.

4. The microfluidic cartridge of claim 1, wherein the homogeneous dissolution of said chromogen defines a first phase of said assay and the reaction of said chromogen with said clinical analyte defines a second phase of said assay; and the first phase and the second phase are separated by a change in sign of the first derivative of said absorbance.

5. The microfluidic cartridge of claim 4, wherein the second phase of said analysis is further defined by a change in absorbance that is zero order for said analyte.

6. The microfluidic cartridge of claim 1, wherein said microfluidic cartridge further comprises a dry substrate, substrates or enzyme for a reaction deposited in said upstream fluidic channel, said dry substrate, substrates, or enzyme further comprising a rehydratable matrix for rapid rehydration in said fluid microsample.

7. The microfluidic cartridge of claim 1, wherein said sample receptacle is a whole blood receptacle, and interposed in said intake channel between said whole blood receptacle and said reaction chamber is a blood filtration element capable of separating plasma from whole blood.

8. The microfluidic cartridge of claim 1, wherein said rehydratable dry reagent matrix comprises a buffer salt and a lyoprotective agent, and said rehydratable dry reagent matrix is printed as a liquid precursor on an inside surface of said optical windows and dried in place.

9. The microfluidic cartridge of claim 1, wherein said apparatus is configured with a chromogen for assay of a clinical analyte by a zero order reaction rate, wherein said analyte is lactate dehydrogenase, creatine phosphokinase, alkaline phosphatase, acid phosphatase, aspartate aminotransferase, alanine aminotransferase, lipase, cholesterol, triglyceride, uric acid, glucose, BUN, creatinine, sodium, potassium, magnesium, phosphorus, calcium, chloride, iron, carbon dioxide, total protein, an antigen, or an antibody.

10. The microfluidic cartridge of claim 1, further comprising an assay circuit arm for endpoint assay of a clinical analyte, wherein said analyte is free hemoglobin, total hemoglobin, bilirubin, an antigen, or an antibody.

11. The microfluidic cartridge of claim 1, wherein the microfluidic cartridge is capable of completing a panel of assays in less than 120 seconds.

12. The microfluidic cartridge of claim 7, wherein said microfluidic cartridge comprises a plurality of assay circuit arms configured for drawing plasma from said whole blood receptacle to each of said plurality of assay circuit arms in series, each assay circuit arm under control of a separate pneumatic circuit of said host workstation.

13. A kit comprising the microfluidic cartridge of claim 1, wherein the microfluidic cartridge is supplied in a sealed foil pouch and requires addition only of said fluid microsample.

14. The kit of claim 13, wherein said fluid microsample is a sample of serum, plasma, whole blood, cerebrospinal fluid, synovial fluid, or urine.

* * * * *